United States Patent
Fernandez et al.

(10) Patent No.: US 10,238,529 B2
(45) Date of Patent: Mar. 26, 2019

(54) OSTOMY BAG

(71) Applicant: 3 West C, LLC, Tyler, TX (US)

(72) Inventors: Luis Fernandez, Tyler, TX (US); James E. Deaton, Georgetown, TX (US); Charles R. Gordon, Tyler, TX (US)

(73) Assignee: 3 West C. LLC, Tyler, TX (US)

( * ) Notice: Subject to any disclaimer, the term of this patent is extended or adjusted under 35 U.S.C. 154(b) by 1203 days.

(21) Appl. No.: 14/498,117

(22) Filed: Sep. 26, 2014

(65) Prior Publication Data

US 2015/0126946 A1    May 7, 2015

Related U.S. Application Data

(60) Provisional application No. 61/883,083, filed on Sep. 26, 2013.

(51) Int. Cl.
*A61F 5/448* (2006.01)

(52) U.S. Cl.
CPC ...... *A61F 5/448* (2013.01); *A61F 2005/4486* (2013.01)

(58) Field of Classification Search
CPC combination set(s) only.
See application file for complete search history.

(56) References Cited

U.S. PATENT DOCUMENTS

| 4,518,389 A | 5/1985 | Steer et al. | 604/339 |
| 4,553,967 A | 11/1985 | Ferguson et al. | 604/317 |
| 4,648,875 A | 3/1987 | Ferguson | 604/339 |
| 4,685,990 A * | 8/1987 | Ferguson | A61F 5/44 156/253 |
| 4,721,508 A * | 1/1988 | Burton | A61F 5/445 604/103.03 |
| 4,834,732 A | 5/1989 | Steer et al. | 604/342 |
| 4,890,608 A * | 1/1990 | Steer | A61F 5/443 602/52 |
| 4,917,691 A * | 4/1990 | Briggs | A61F 5/448 604/339 |
| 4,929,245 A | 5/1990 | Holtermann et al. | 604/338 |
| 5,041,102 A | 8/1991 | Steer et al. | 604/338 |
| 5,180,377 A | 1/1993 | Holtermann | 604/342 |
| 5,250,042 A | 10/1993 | Torgalkar et al. | 604/333 |
| 5,257,981 A * | 11/1993 | Takahashi | A61F 5/448 604/332 |
| 5,322,526 A | 6/1994 | Nakamura et al. | 505/330 |
| 5,647,861 A * | 7/1997 | Steer | A61F 5/448 215/279 |

(Continued)

OTHER PUBLICATIONS

International Search Report and Written Opinion issued in PCT/US2014/057725 dated Feb. 24, 2015.

*Primary Examiner* — Tatyana Zalukaeva
*Assistant Examiner* — Guy K Townsend
(74) *Attorney, Agent, or Firm* — Norton Rose Fulbright US LLP (57) ABSTRACT

An ostomy bag for receiving waste from a patient's stoma. The ostomy bag may include a finger probe for allowing a user to manually manipulate the stoma to clear blockages of the stoma. The ostomy bag may also include a stoma port for attachment to the patient's skin surrounding the stoma. A mating collar on the ostomy bag sealingly attaches the ostomy bag to the stoma port using a convenient quarter turn connection.

12 Claims, 7 Drawing Sheets

(56) References Cited

U.S. PATENT DOCUMENTS

| | | | | |
|---|---|---|---|---|
| 5,662,629 A * | 9/1997 | Steer | ............ | A61F 5/448 215/274 |
| 5,693,035 A | 12/1997 | Leise et al. | ............ | 604/333 |
| 5,709,674 A * | 1/1998 | Steer | ............ | A61F 5/448 604/332 |
| 5,843,053 A * | 12/1998 | Steer | ............ | A61F 5/448 604/342 |
| 5,961,501 A | 10/1999 | Cassidy et al. | ............ | 604/327 |
| 5,976,118 A * | 11/1999 | Steer | ............ | A61F 5/441 604/332 |
| 6,106,507 A * | 8/2000 | Botten | ............ | A61F 5/448 604/336 |
| 6,409,710 B1 | 6/2002 | Holtermann | ............ | 604/342 |
| 6,506,184 B1 | 1/2003 | Villefrance | ............ | 604/333 |
| 6,569,134 B1 * | 5/2003 | Leise, Jr. | ............ | A61F 5/448 604/332 |
| 6,709,422 B2 * | 3/2004 | Hessel | ............ | A61F 5/448 604/342 |
| 6,712,800 B2 | 3/2004 | Kanbara | ............ | 604/333 |
| 6,773,420 B2 | 8/2004 | Kanbara | ............ | 604/333 |
| 7,347,844 B2 * | 3/2008 | Cline | ............ | A61F 5/445 604/336 |
| 7,789,866 B2 | 9/2010 | Poulsen et al. | ............ | 604/333 |
| 8,007,483 B2 | 8/2011 | Worsoee | ............ | 604/333 |
| 8,142,406 B2 | 3/2012 | Blum | ............ | 604/338 |
| 8,343,121 B2 * | 1/2013 | Cramer | ............ | A61F 5/445 604/334 |
| 8,439,883 B1 * | 5/2013 | Johnsen | ............ | A61F 5/448 604/338 |
| 8,708,987 B2 * | 4/2014 | Cramer | ............ | A61F 5/443 604/344 |
| 9,498,372 B2 * | 11/2016 | Fattman | ............ | A61F 5/448 |
| 9,517,157 B2 * | 12/2016 | Hanuka | ............ | A61F 5/4401 |
| 2002/0165507 A1 * | 11/2002 | Hessel | ............ | A61F 5/448 604/342 |
| 2004/0184876 A1 * | 9/2004 | Hessel | ............ | A61F 5/448 403/326 |
| 2004/0193122 A1 * | 9/2004 | Cline | ............ | A61F 5/445 604/332 |
| 2004/0223944 A1 * | 11/2004 | Capelli | ............ | A61K 33/38 424/78.1 |
| 2005/0177119 A1 * | 8/2005 | Tsai | ............ | A61F 5/445 604/332 |
| 2006/0184145 A1 * | 8/2006 | Ciok | ............ | A61F 5/443 604/338 |
| 2006/0200101 A1 * | 9/2006 | Mullejans | ............ | A61F 5/441 604/339 |
| 2008/0071237 A1 * | 3/2008 | Chen | ............ | A61F 5/451 604/352 |
| 2011/0213322 A1 * | 9/2011 | Cramer | ............ | A61F 5/443 604/344 |
| 2011/0238024 A1 * | 9/2011 | Smith | ............ | A61F 5/445 604/336 |
| 2013/0138062 A1 * | 5/2013 | Klein | ............ | A61F 5/443 604/336 |
| 2013/0304008 A1 * | 11/2013 | Hanuka | ............ | A61F 5/4401 604/334 |
| 2014/0148771 A1 * | 5/2014 | Luce | ............ | A61F 5/445 604/345 |
| 2015/0126946 A1 * | 5/2015 | Fernandez | ............ | A61F 5/448 604/342 |
| 2015/0265455 A1 * | 9/2015 | Fernandez | ............ | A61F 5/448 604/342 |
| 2015/0305916 A1 * | 10/2015 | Hanuka | ............ | A61F 5/4401 604/333 |
| 2015/0320585 A1 * | 11/2015 | Fattman | ............ | A61F 5/445 604/344 |

* cited by examiner

OSTOMY BAG

CROSS-REFERENCE TO RELATED APPLICATIONS

This application claims priority to U.S. Provisional Application No. 61/883,083, filed Sep. 26, 2013, the entire contents of which is specifically incorporated by reference herein without disclaimer.

BACKGROUND

1. Field of the Invention

The present invention relates to an ostomy bag for receiving waste from a patient's stoma.

2. Description of Related Art

An ostomy is a surgical procedure to create an opening (stoma) from an area inside the body to the outside. It is used to treat certain diseases of the digestive or urinary systems. It can be permanent or temporary. Three common ostomies are a colostomy, an ileostomy and an urostomy. In a colostomy, a stoma is formed in a patient's abdominal wall and the colon is attached to the stoma. In an ileostomy, a stoma is formed in a patient's abdominal wall and the bottom of the small intestine (i.e., the ileum) is attached to the stoma. In an urostomy, a stoma is formed in a patient's abdominal wall and a passage is created to allow urine to flow outside of the body.

Waste is discharged from the stoma, and the patient must wear an ostomy bag to collect the waste material. A wide variety of ostomy bags are in general use today. However, these bags suffer from various issues and there is a need for an improved ostomy bag.

SUMMARY

An improved ostomy bag is disclosed. In accordance with one embodiment, an ostomy bag comprises a bag member having an interior chamber for receiving waste from a patient's stoma and an opening for attachment to the patient's stoma. A finger probe is attached to the bag member, and the finger probe is configured to allow the patient to manipulate the stoma to clear blockages and the like. The finger probe may comprise a pouch attached to the bag member. The bag member may include a resealable opening for draining the bag.

The ostomy bag may further comprise a stoma port and a locking ring for sealing the opening in the bag member to the stoma port. The stoma port may be attached to the skin surrounding the stoma and has an opening therethrough and threads on an outer surface for engaging the locking ring. The stoma port may comprise a first mating surface and the locking ring may comprise a second mating surface for engaging the first mating surface to seal the bag to the stoma port. An o-ring may be disposed on one of the first and second mating surfaces. The locking ring may comprise at least one locking tab for engaging at least one locking recess disposed on the stoma port. The ostomy bag may be formed of an antimicrobial material, and the antimicrobial material may comprise silver. A locking cap for sealing the stoma port may be provided. A stoma bag for facilitating changing of the ostomy bag may be provided. The stoma bag may comprise a bag with a sealing ring for sealing the bag to the stoma.

In accordance with another exemplary embodiment, an ostomy bag for use with a stoma port attached to a patient's stoma is provided. The stoma port comprises a first mating surface with an aperture for passing waste from the patient's stoma therethrough. The ostomy bag comprises a bag having an interior chamber and an opening for receiving waste from a patient's stoma. A locking collar is disposed around the opening, and the locking collar forms a second mating surface configured for attachment to the first mating surface. The ostomy bag may further comprise an o-ring disposed in a recess on one of the first and second mating surfaces. The locking collar may comprise a threaded locking nut disposed around the opening for attachment to the stoma port. The locking nut may be fully engaged with a quarter turn. The locking nut may comprise at least one locking tab for engaging at least one locking recess disposed on the stoma port. The ostomy bag may further comprise a finger probe configured to allow the patient to manipulate the stoma to clear blockages. The finger probe may comprise a pouch attached to the bag member. The ostomy bag may comprise an antimicrobial material, and the antimicrobial material may comprise silver. A stoma bag for facilitating changing of the ostomy bag may be provided. The stoma bag may comprise a bag with a sealing ring for sealing the bag to the stoma.

The term "coupled" is defined as connected, although not necessarily directly. The terms "a" and "an" are defined as one or more unless this disclosure explicitly requires otherwise.

The terms "substantially," "approximately," and "about" are defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, or a component of a system, that "comprises," "has," "includes" or "contains" one or more elements or features possesses those one or more elements or features, but is not limited to possessing only those elements or features. Likewise, a method that "comprises," "has," "includes" or "contains" one or more steps possesses those one or more steps, but is not limited to possessing only those one or more steps. Additionally, terms such as "first" and "second" are used only to differentiate structures or features, and not to limit the different structures or features to a particular order.

A device, system, or component of either that is configured in a certain way is configured in at least that way, but it can also be configured in other ways than those specifically described.

Any embodiment of any of the systems and methods can consist of or consist essentially of—rather than comprise/include/contain/have—any of the described elements, features, and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Details associated with the embodiments described above and others are presented below.

DESCRIPTION OF ILLUSTRATIVE EMBODIMENTS

In the following detailed description, reference is made to the accompanying drawings, in which are shown exemplary but non-limiting and non-exhaustive embodiments of the invention. These embodiments are described in sufficient detail to enable those having skill in the art to practice the invention, and it is understood that other embodiments may be used, and other changes may be made, without departing from the spirit or scope of the invention. The following detailed description is, therefore, not to be taken in a limiting sense, and the scope of the invention is defined only by the appended claims. In the accompanying drawings, like reference numerals refer to like parts throughout the various figures unless otherwise specified.

Referring to FIGS. 1-5, an ostomy bag 100 comprises a bag member 102 with an interior cavity 104 for receiving waste from a patient's stoma 106 through an opening 108. Bag member 102 may be formed of any liquid impermeable material, such as polyvinyl chloride, and may be constructed using any conventional manufacturing technique. In one embodiment, ostomy bag 100 is assembled using multiple pieces which are solvent welded together. Ostomy bag 100 may include an antimicrobial agent coated on or embedded in the material. In one embodiment, the antimicrobial agent is silver, such as silver nanoparticles, which have well known antimicrobial properties.

Ostomy bag 100 may be utilized with any type of ostomy. In certain embodiments, it is adapted for use with a colostomy or an ileostomy.

Figure 1:
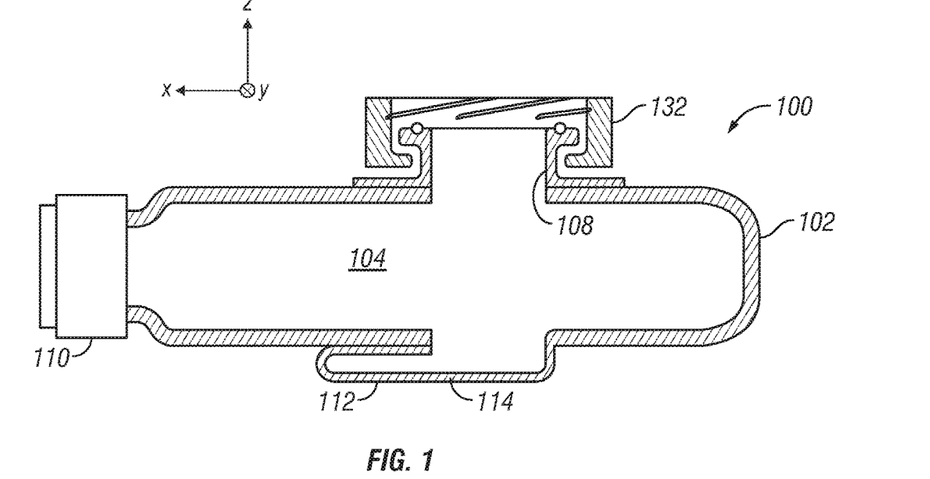
FIG. 1 is a sectional diagram of an ostomy bag in accordance with an embodiment of the present invention.

Ostomy bag 100 may be drainable or a disposable. A drainable ostomy bag includes a resealable opening 110 for draining ostomy bag 100. In one embodiment, resealable opening 110 comprises a tail which may be rolled up to seal the tail, which is then held shut with a closure strip. In another embodiment, resealable opening 110 comprises a threaded circular opening which may be covered with a threaded cap. Ostomy bag 100 may also include a vent (not illustrated) to allow gases to exit ostomy bag 100. In certain embodiments, the vent includes odor control agents, such as activated charcoal.

Figure 2:
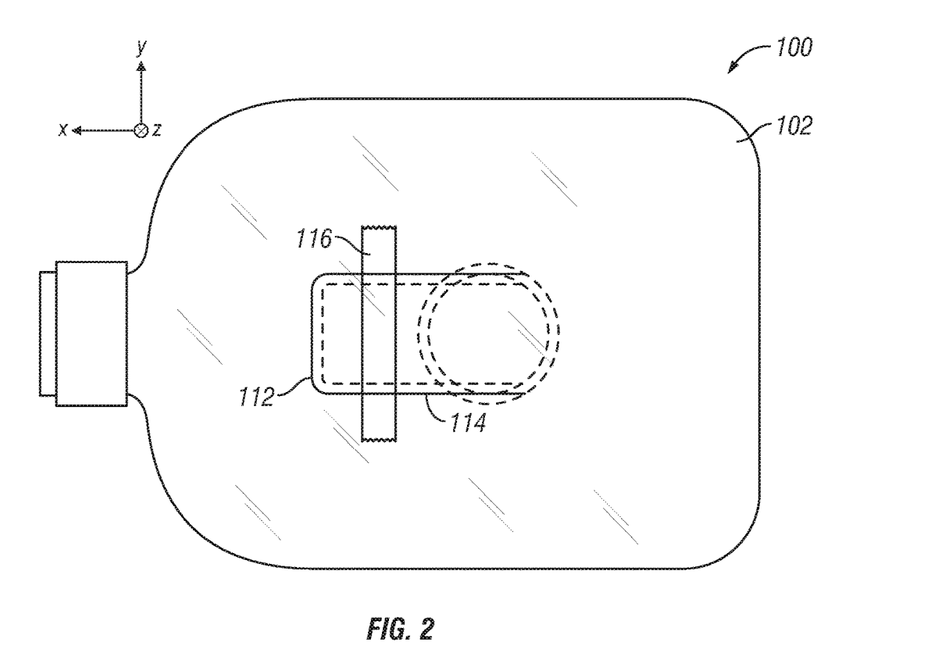
FIG. 2 is a plan view of the ostomy bag of FIG. 1.

Ostomy bag 100 may include a finger probe or flap 112 to allow a user to manually manipulate a stoma. For example, if stoma 106 has a blockage, a user may insert his finger into finger probe 112 and remove the blockage without having to remove ostomy bag 100. In one embodiment, finger probe 112 comprises an elongate tube 114 which is sealed at one end and open to the interior of ostomy bag 100 at the other end. Finger probe 112 may be formed of the same material as the bag member of ostomy bag 100, or may be formed of thinner material to allow easier manipulation or stronger material to withstand repeated manipulation of the material without breakage. When not in use, finger probe 112 may be fastened to ostomy bag 100 using a closure strip 116. Closure strip 116 may comprise a refastenable material, such as hook and loop fasteners, or tape.

Figure 3:
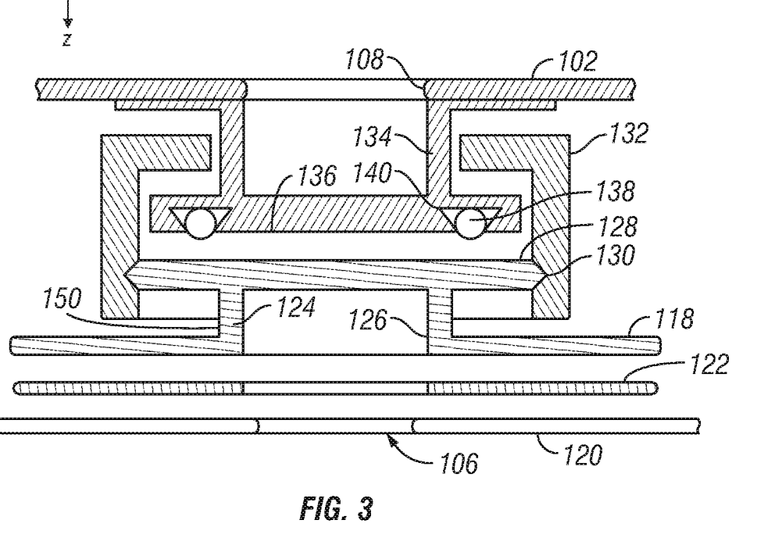
FIG. 3 is an enlarged section diagram of a stoma port and locking ring of the ostomy bag of FIG. 1.
Figure 4:
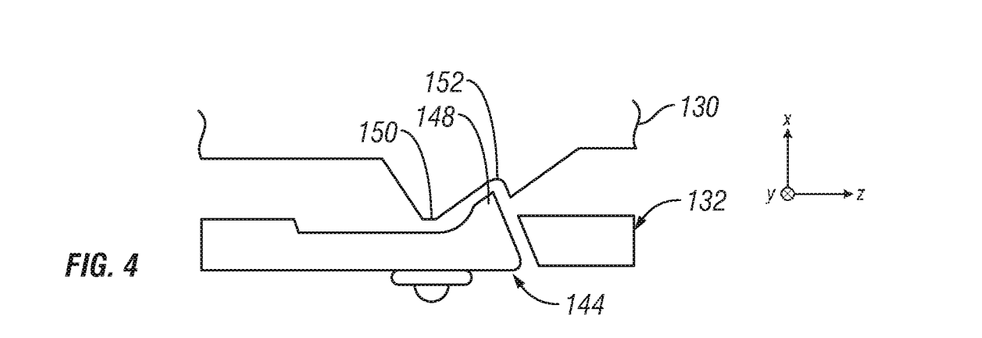
FIG. 4 is a sectional view of a quarter turn snap lock in accordance with an embodiment of FIG. 1.

Ostomy bag 100 may be adapted to mate with a stoma port 118. Stoma port 118 is attached to the skin 120 surrounding stoma 106 using a gasket 122 with adhesive on both sides or the like. Stoma paste or similar material may be used to seal any openings which remain between the port and the patient's skin. Stoma port 118 may be left in place for an extended period of time, such as several days. This allows a patient to conveniently change ostomy bag 100 without the time-consuming process of preparing the surrounding skin 120 and adhering a new bag directly to the prepared skin 120.

In one embodiment, stoma port 118 comprises a skin facing surface member 124 with an opening 126 therethrough. Opening 126 in stoma port 118 is placed over patient's stoma 106 so that waste may flow from stoma 106 and through stoma port 118. In an embodiment, skin facing surface member 124 has a low profile and is formed of a plastic material which is comfortable for a patient to wear for an extended period of time.

A conduit 150 extends from skin facing surface member 124 to a mating surface 128. Conduit 150 conveys waste from opening 126 in stoma port 118 to mating surface 128. The conduit is typically short so that the patient does not have items protruding from the area of the stoma (e.g., the abdominal wall). In certain embodiments, mating surface 128 is flat. The outer circumference of the mating surface 128 forms threads 130 for connection with a locking retainer 132.

A flange member 134 is coupled to bag member 102 and has an opening for passing waste through flange member 134. A mating surface 136 on flange member 134 is configured to mate with mating surface 128 of stoma port 118. In certain embodiments, the mating surfaces 128, 136 are flat. However, they may also be configured in any other complementary shape. In certain embodiments, the mating surfaces 128, 136 further comprise an o-ring 138 arranged in a recess 140 in one of the mating surfaces. Recess 140 may comprise a dovetail slot in the face of mating surface 136 on flange member 134.

A locking retainer 132 is provided to securely attach bag member 102 to stoma port 118. Locking retainer 132 may comprise a locking nut which surrounds flange member 134 on bag member 102. It should be noted that the gaps in FIG. 3 are exaggerated for clarity. Locking member 132 has internal threads which cooperate with external threads 130 on stoma port 118. Preferably, the threads are configured so that bag member 102 may be attached to and detached from stoma port 118 with a quarter turn.

Figure 5:
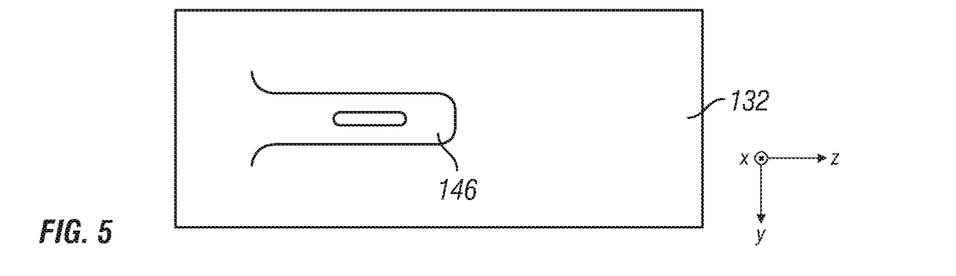
FIG. 5 is a side view of the quarter turn snap lock illustrated in FIG. 3.
Figure 6:
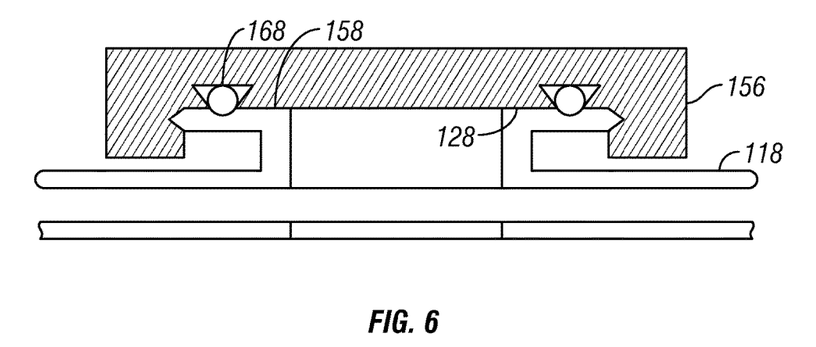
FIG. 6 is a section diagram of a cap for covering the stoma port of FIG. 3.

Locking retainer 132 may include a snap lock 144 to securely fasten it to stoma port 118 and minimize the chances of inadvertently releasing bag member 102 from stoma port 118. As seen in FIGS. 5 and 6, the locking retainer 132 has a flexible tongue 146 with a protrusion 148. The threads on stoma port 118 contains a ramp 150 with a recess 152. When locking retainer 132 is rotated into position, protrusion 148 is guided by ramp 150 and snaps into recess 152 to provide a positive lock. In some embodiments, tongue 146 makes an audible click to provide feedback to the user. Snap lock 144 may be disengaged by pressing on the back side of flexible tongue 146, which levers protrusion 148 out of recess 152 and allows locking retainer 132 to be reversed and removed.

As seen in FIG. 6, a cap member 156 may be provided to facilitate changing of the colostomy bag. The patient is unable to control discharge of waste from stoma 106, and waste may leak from stoma 106 while the patient is changing ostomy bag 100. To prevent this leakage, a cap member 156 may be provided to place on stoma port 118 while changing the bag. Cap member 156 has a similar construction to locking retainer 132. In the illustration of FIG. 6, cap member 156 is tightened so that stoma port mating surface 128 and cap mating surface 158 are pressed against one another and o-ring 168 is compressed to form a tight seal. Cap member 156 may be fully engaged with a quarter turn lock, and may use a locking retainer as previously described.

Figure 7:
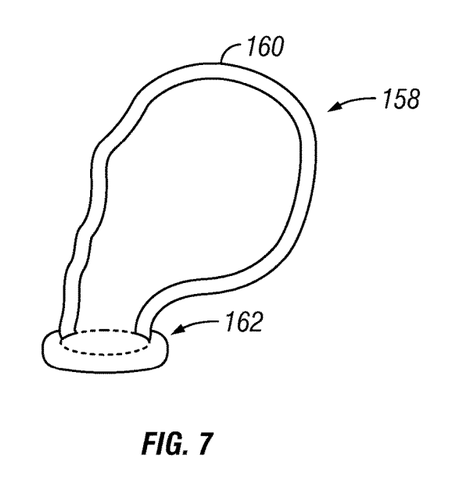
FIG. 7 is a side view of a stoma pouch for changing a colostomy bag.
Figure 8:
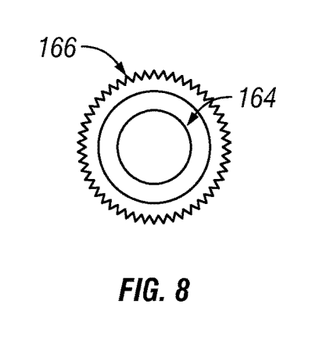
FIG. 8 is a bottom view of the stoma pouch of FIG. 7.
Figure 9:
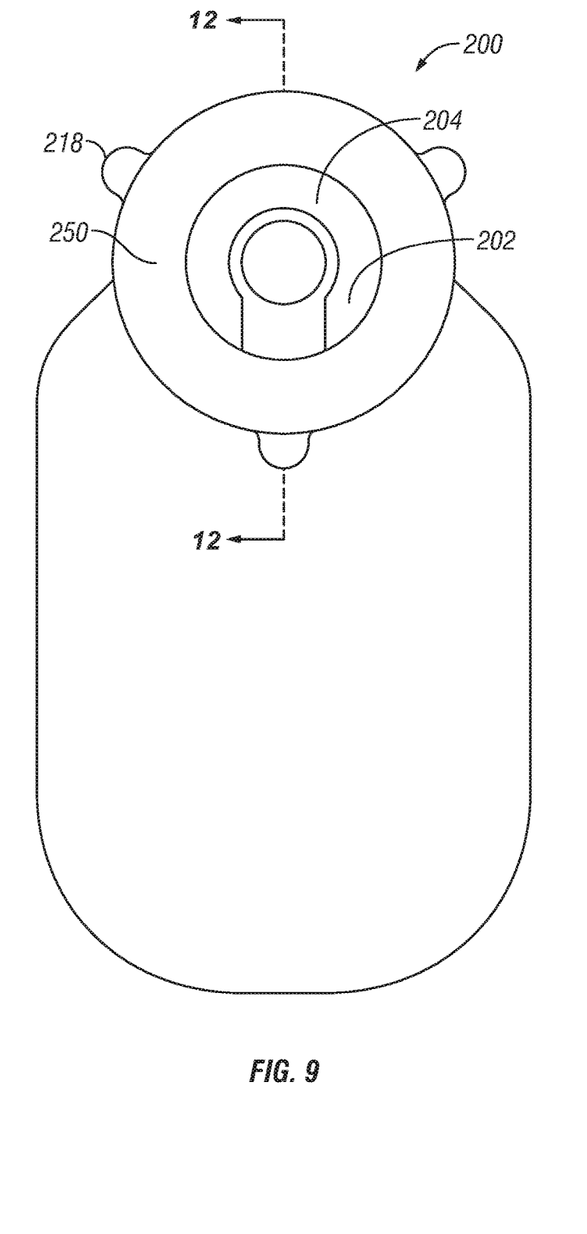
FIG. 9 is a plan view of an ostomy bag in accordance with an embodiment of the present invention.
Figure 10:
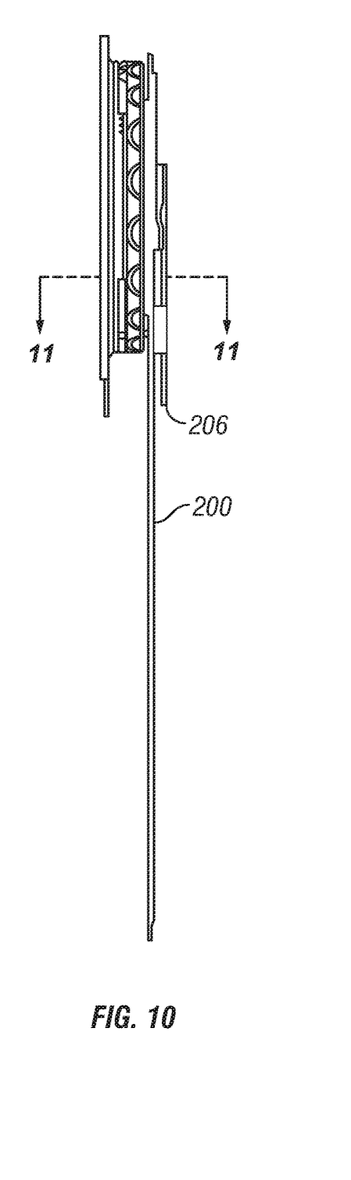
FIG. 10 is a side view of the ostomy bag of FIG. 9.
Figure 11:
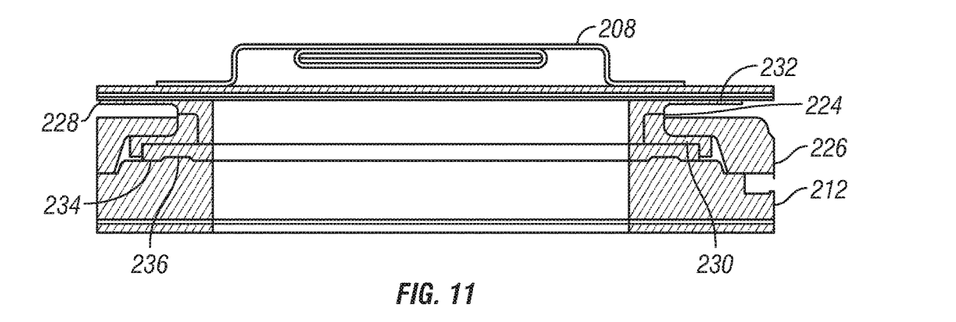
FIG. 11 is a sectional view taken along line 11-11 in FIG. 9.
Figure 12:
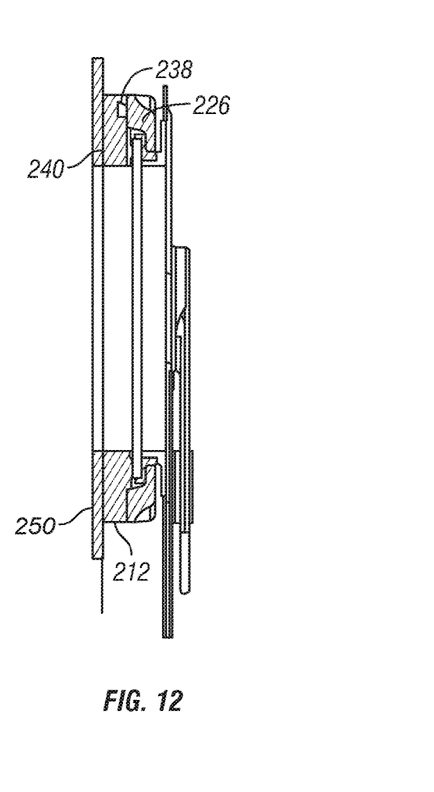
FIG. 12 is a sectional view taken along line 12-12 in FIG. 9.

As seen in FIGS. 7 and 8, a stoma bag 158 may be provided to facilitate changing of the stoma port 118. Since the patient is unable to control discharge of waste from stoma 106, stoma bag 158 may be placed over the stoma 106 while changing the stoma port 118 to capture any waste discharged from the stoma 106. Stoma bag 158 comprises a bag member 160 formed of a liquid impermeable material and a sealing ring 162 for sealing the bag member 160 to stoma 106. Sealing ring 162 contains an inner ring 164 of a soft, pliable material that may be pressed against stoma 106 to temporarily seal sealing ring 162 against stoma 106. One suitable material is a soft foam material. An adjustable layer 166 is formed on the outside of the inner ring 164. Adjustable layer 166 provides tension to hold sealing ring 162 against stoma 106. Adjustable layer 166 may comprise an elastic material or may use a drawstring.

Referring to FIGS. 9-16, another embodiment of an ostomy bag 200 comprises a bag member 200 with an interior cavity 202 for receiving waste from a patient's stoma through an opening 204. Ostomy bag 200 may include a finger probe or flap 206 to allow a user to manually manipulate a stoma, as described above. A strap 208 may be provided to hold the finger probe in place when not in use.

Figure 13:
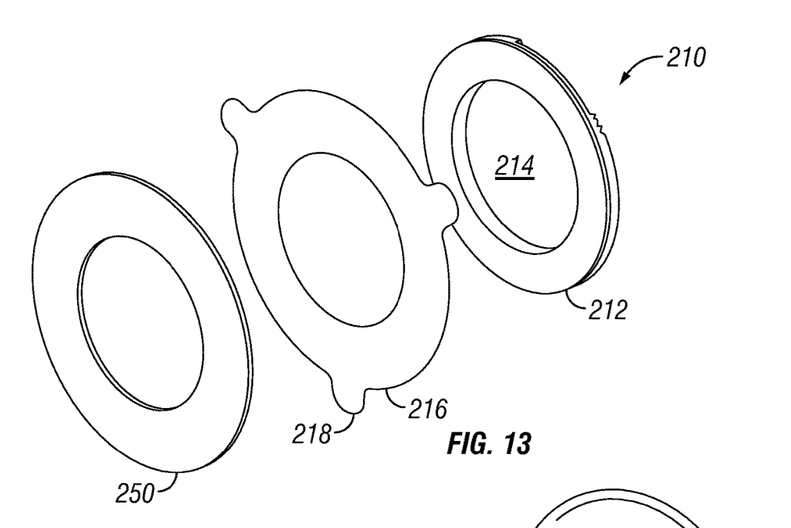
FIG. 13 is an exploded assembly view of a stoma port of the ostomy bag of FIG. 9.

Ostomy bag 200 may be adapted to mate with a stoma port 210. Stoma port 210 comprises a stoma port ring 212 with an opening 214 therethrough, a stoma port removal ring 216 coupled to stoma port ring 212, and an adhesive foam gasket 250. Stoma port removal ring 216 has outwardly extending tabs 218 to allow a user to grasp stoma port 210 to aid in holding in place during bag installation and removal. Opening 214 in stoma port 210 is placed over a patient's stoma and adhered to the patient's skin with adhesive gasket 250 so that waste may flow from the stoma and through stoma port 210. In an embodiment, stoma port 210 has a low profile and is formed of a plastic material which is comfortable for a patient to wear for an extended period of time.

Figure 14:
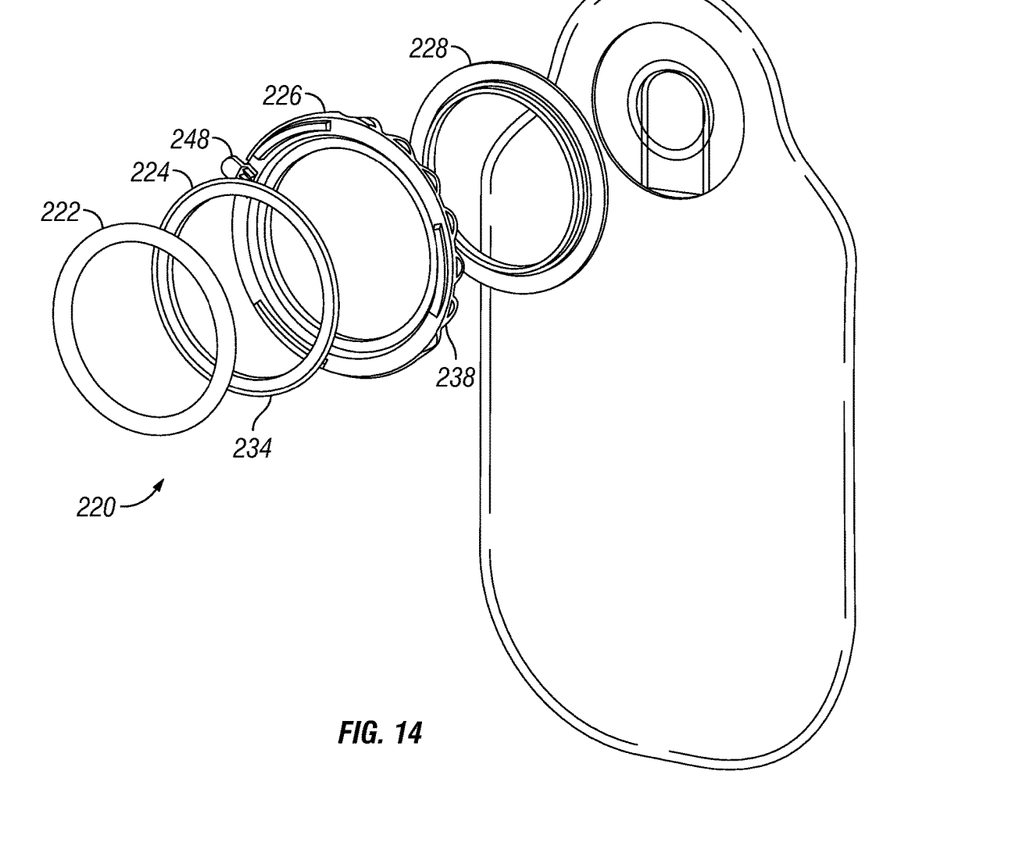
FIG. 14 is an exploded assembly view of the ostomy bag of FIG. 9.
Figure 15:
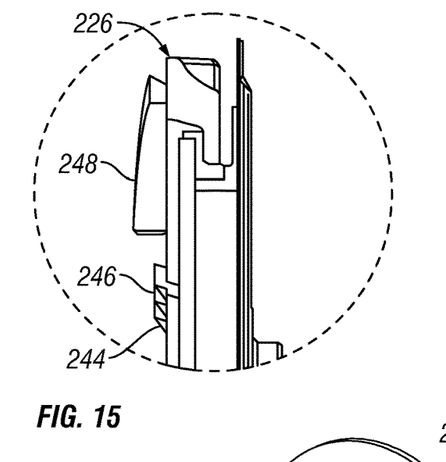
FIG. 15 is a detail view of the assembly of the ring assembly to the bag member of the ostomy bag of FIG. 9.
Figure 16:
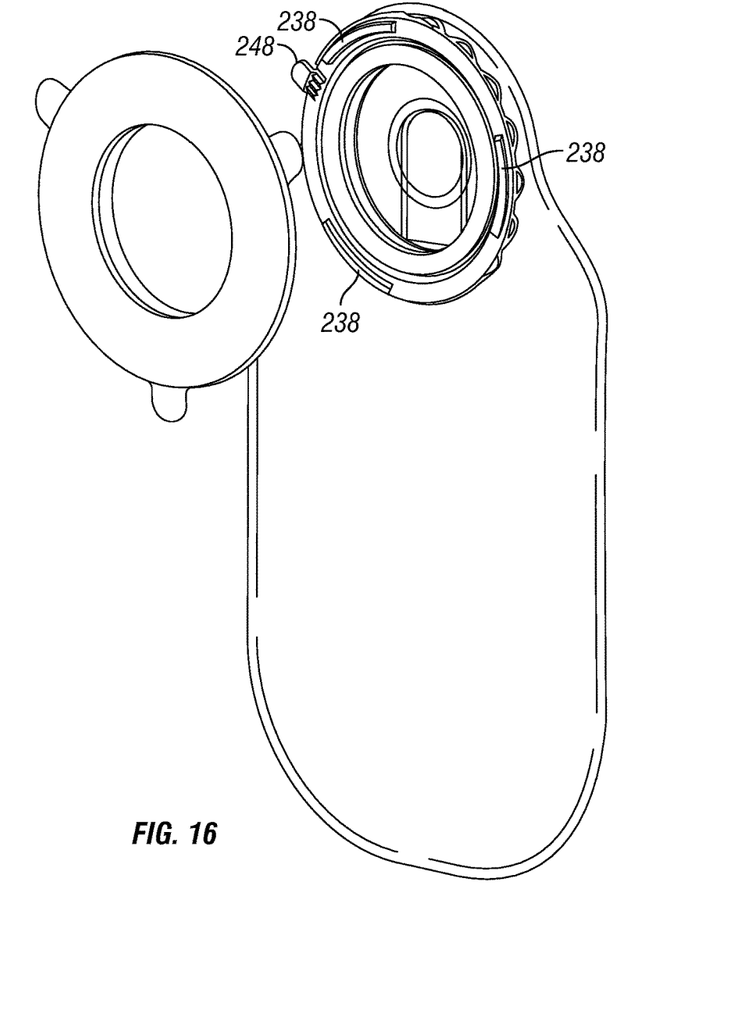
FIG. 16 is a perspective view of the stoma port and ostomy bag of FIG. 9.

Ostomy bag 200 has a ring assembly 220 that mates with stoma port 210. Ring assembly 220 comprises a gasket seal 222, and interface ring 224, a locking ring 226 and a bag ring 228. Bag ring 228 is coupled to the bag member 202. Locking ring 226 is placed over the bag ring 228, and interface ring 226 is coupled to bag ring 228 to capture locking ring 226 between the flanges 230, 232 at the edges of interface ring 224 and bag ring 228.

Interface ring 224 and stoma port ring 212 may have opposed surfaces 234, 236. Gasket 222 may be disposed between locking 226 and interface ring 224 to provide a substantially fluid tight connection. Locking ring 226 may have one or more face threads 238 which correspond with complementary threads 240 in stoma port 210 (see FIG. 12). In the exemplary embodiment shown, face threads 138 are dovetail shaped, and complementary threads 240 have an opening portion and a mating portion 242. The face threads 138 are inserted into the opening and then rotated into the mating portion 242 to couple interface ring 224 to stoma port ring 212. This face thread assembly helps produce a lower profile, which increases patient comfort. A locking assembly 242 may be provided to hold interface ring 224 in place with respect to stoma port ring 212. In one embodiment, locking assembly 242 comprises a pair of mating sawtooth profiles 244, 246. Sawtooth profiles 244, 246 may be disengaged from one another by manipulating locking tab 248 to allow removal of ostomy bag 200.

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices are not intended to be limited to the particular forms disclosed. Rather, they include all modifications and alternatives falling within the scope of the claims, and embodiments other than the one shown may include some or all of the features of the depicted embodiment. For example, components may be combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

What is claimed is:

1. An ostomy bag for use with a stoma port attached to a patient's stoma, the stoma port comprising a first mating surface with an aperture for passing waste from the patient's stoma therethrough, the ostomy bag comprising:
- a bag having an interior chamber and an opening for receiving waste from a patient's stoma; and
- a locking ring defining an opening and configured to be disposed around the opening of the bag such that opening of the locking ring is in fluid communication with the opening of the bag, the locking ring comprising:
  - a second mating surface configured for attachment to the first mating surface; and
  - at least one projection extending from the second mating surface, the at least one projection having:
    - a length measured in a direction extending circumferentially around the opening of the locking ring;
    - a height measured in a direction that is normal to the second mating surface;
    - a first thickness measured in a direction that is perpendicular to the direction of the height; and
    - a second thickness measured in a direction that is perpendicular to the direction of the height, the second thickness being greater than the first thickness and the second thickness being farther from the second mating surface than the first thickness.

2. The ostomy bag according to claim 1, further comprising a gasket for sealing the locking ring to the stoma port.

3. The ostomy bag according to claim 2, wherein the gasket comprises an o-ring configured to be disposed between the first and second mating surfaces.

4. The ostomy bag according to claim 1, wherein the bag comprises a finger probe configured to allow the patient to manipulate the stoma.

5. The ostomy bag according to claim 4, wherein the finger probe comprises a pouch attached to the bag.

6. The ostomy bag according to claim 1, wherein the bag comprises an antimicrobial agent.

7. The ostomy bag according to claim 6, wherein the antimicrobial agent comprises silver.

8. The ostomy bag according to claim 1, comprising a threaded locking nut configured to releasably secure the locking ring to the bag.

9. The ostomy bag according to claim 1, wherein the height of the at least one projection changes along the length.

10. The ostomy bag according to claim 1, wherein:
- the stoma port defines an aperture configured to be in fluid communication with the opening of the bag;
- the first mating surface encircles the aperture of the stoma port; and
- the stoma port includes a groove recessed from the first mating surface and extending circumferentially around at least a portion of the aperture, the groove being configured to receive the at least one projection of the locking ring such that:
  - rotational movement of the locking ring relative to the stoma port in a first direction secures the bag to the stoma port; and
  - rotational movement of the locking ring relative to the stoma port in a second direction opposite the first direction permits the decoupling of the bag from the stoma port.

11. The ostomy bag according to claim 10, wherein:
- the stoma port includes at least one latching protrusion;
- the locking ring includes at least one latching protrusion configured to be received by the at least one latching protrusion of the stoma port such that:
  - upon rotational movement of the locking ring relative to the stoma port in the first direction, the corresponding latching protrusions of the stoma port and locking ring engage to secure the bag to the stoma port.

12. The ostomy bag according to claim 11, wherein the locking ring includes a release tab that is manipulatable to disengage the corresponding latching protrusions of the stoma port and the locking ring, thereby permitting rotational movement of the locking ring relative to the stoma port in the second direction to decouple the bag from the stoma port.

* * * * *